(12) United States Patent
Hacco et al.

(10) Patent No.: US 9,597,526 B2
(45) Date of Patent: Mar. 21, 2017

(54) FLEXIBLE LIGHT TREATMENT HEAD

(75) Inventors: Eli Hacco, Toronto (CA); Nicholas John Molo, Oakville (CA); Li Che Teddy Chen, North York (CA)

(73) Assignee: Meditech International Inc., Toronto (CA)

( * ) Notice: Subject to any disclaimer, the term of this patent is extended or adjusted under 35 U.S.C. 154(b) by 457 days.

(21) Appl. No.: 13/355,162

(22) Filed: Jan. 20, 2012

(65) Prior Publication Data
US 2013/0190842 A1 Jul. 25, 2013

(51) Int. Cl.
*A61N 5/06* (2006.01)

(52) U.S. Cl.
CPC ........ *A61N 5/06* (2013.01); *A61N 2005/0633* (2013.01); *A61N 2005/0645* (2013.01); *A61N 2005/0652* (2013.01)

(58) Field of Classification Search
CPC .................................. A61N 5/06; A61B 18/20
See application file for complete search history.

(56) References Cited

U.S. PATENT DOCUMENTS

| | | | |
|---|---|---|---|
| 3,068,668 A * | 12/1962 | Buchleitner | 464/173 |
| 6,187,029 B1 * | 2/2001 | Shapiro et al. | 607/88 |
| 6,221,095 B1 * | 4/2001 | Van Zuylen et al. | 607/88 |
| 2005/0085875 A1 | 4/2005 | Van Zuylen | |
| 2006/0200213 A1 | 9/2006 | McDaniel | |
| 2006/0282134 A1 * | 12/2006 | Shapiro et al. | 607/88 |
| 2006/0287696 A1 | 12/2006 | Wright | |
| 2007/0129778 A1 | 6/2007 | Dougal | |
| 2007/0233208 A1 | 10/2007 | Kurtz et al. | |
| 2008/0179879 A1 * | 7/2008 | Wu | 285/148.1 |
| 2011/0106222 A1 * | 5/2011 | Wilson et al. | 607/88 |
| 2012/0008042 A1 * | 1/2012 | Wang et al. | 348/373 |
| 2012/0148976 A1 * | 6/2012 | Brawn | A61C 7/06 433/24 |
| 2013/0041434 A1 | 2/2013 | Youn | |
| 2013/0178764 A1 | 7/2013 | Eckhouse | |

FOREIGN PATENT DOCUMENTS

WO 2010064035 A1 6/2010

OTHER PUBLICATIONS

IMI Products LEP2000, LD200; Mar. 23, 2011; International Medical Instruments Inc.; http://home.interlog.com/~imi/products.htm.
Extended European Search Report issued in corresponding EP Application No. 13889643; search completed Jan. 27, 2017.

* cited by examiner

*Primary Examiner* — Lynsey Crandall
(74) *Attorney, Agent, or Firm* — Blake, Cassels & Graydon LLP; Wilfred P. So

(57) ABSTRACT

A flexible light treatment head comprising one or more light source modules interconnected by a hinge apparatus along a flexing edge thereof. The light source modules have light emitting elements, such as LEDs or LASERs. The hinge apparatus comprises one or more hinges. Each hinge has a head wiring channel disposed to form a continuous wiring channel along the hinge apparatus. A head wiring channel is also provided for routing wires into the light source module.

17 Claims, 10 Drawing Sheets

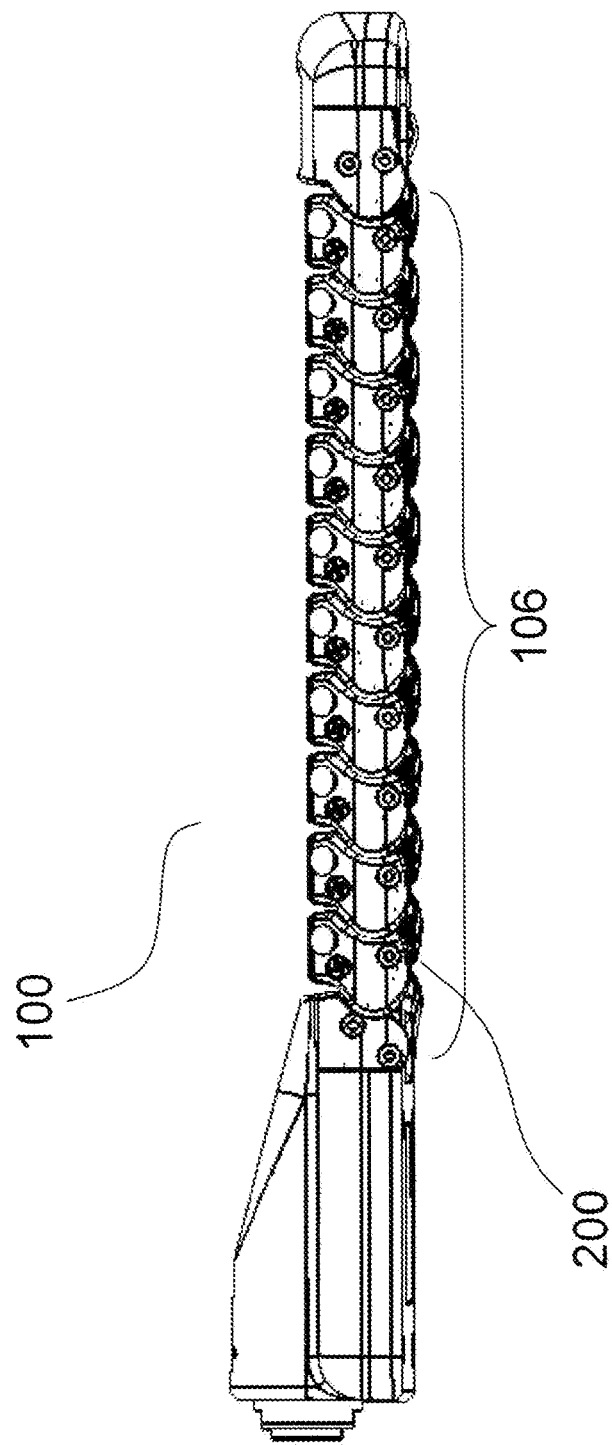

FLEXIBLE LIGHT TREATMENT HEAD

FIELD OF THE INVENTION

The present invention relates generally to the field of light treatment therapy and more specifically to a flexible light treatment head for such therapy.

DESCRIPTION OF THE PRIOR ART

Light treatment of patients for various conditions is becoming well known. Light treatment of injuries such as: sport injuries, sprains and the like; chronic conditions such as arthritis, sciatica and various related conditions; and chronic slow healing wounds or sores, are all well known.

The principle of all these light treatments is the application of low intensity light radiating in the area of the patient's condition. It is found that in order to be effective, the light source should be in close contact with the skin. The light source is usually an array or panel of low intensity light emitting diodes, or in some cases low level laser. The treatment typically becomes more effective over longer periods. The light sources may, for example, be left in contact with the skin for thirty to sixty minutes. This enables deep penetration of the light rays into the tissues, and may produce the healing results experienced.

Another factor in the design of such treatment head is that the treatment might be desired over a large and contoured (non-planar) area of the body. Light treatment heads may measure about four inches by ten or more inches. However, at these dimensions, or if a larger light treatment head is desired, there are numerous shortcomings of particular existing light treatment heads.

For example, rigid light treatment heads are typically not provided in a dimension larger than a few inches square, since there are no correspondingly large planar body parts to be treated.

To overcome this issue, several flexible light treatment heads have been proposed. There are several shortcomings of some existing flexible light treatment heads. Some such flexible light treatment heads are biased to an unflexed (planar) position. Thus, to maintain the flexing of the head during treatment, the head is usually strapped to a patient. The bias of the head can then cause the strap to pull on the patient's body in the precise area at which the patient is suffering. This has been shown to cause discomfort and pain to a patient being treated. Another shortcoming is that other flexible light treatment heads are flimsy as a result of their design.

Furthermore, some flexible light treatment heads are not adaptable to sizes much larger than a few inches square. Other flexible light treatment heads are designed in a way to cause significant barriers to repair, when they are found to be faulty or damaged.

It is an object of the present invention to obviate or mitigate at least one of the above disadvantages.

SUMMARY OF THE INVENTION

In one aspect, the present invention provides a flexible light treatment head comprising one or more light source modules interconnected by a hinge apparatus along a flexing edge thereof. The hinge apparatus may comprise a plurality of hinge joints.

In another aspect, each hinge joint may be substantially identical. In an embodiment, each hinge joint may have a first end and a second end, said first end adapted to fit rotatably in a corresponding second end of an adjacent hinge joint. In an embodiment, each hinge joint may comprise a head wiring channel disposed from said first end to said second end. In an embodiment, each hinge joint may comprise a module wiring channel extending from said head wiring channel. In an embodiment, the module wiring channel may extend substantially perpendicularly from said head wiring channel.

In an embodiment, the hinge apparatus may provide a radius of curvature of 20 mm concavely and 87 mm convexly with reference to a treatment surface of said flexible light treatment head. In an embodiment, the hinge apparatus may be unbiased. In an embodiment, the hinge joint may rotate along only one axis relative to an adjacent hinge joint. In an embodiment, a hinge joint cover may be disposed along an outer surface of the hinge joint. In an embodiment, the hinge joint cover may be removable to diagnose and repair said flexible light treatment head.

In yet another aspect, the flexible light treatment head further comprises a proximal strap aperture adapted to engage a strap. In an embodiment, the flexible light treatment head may further comprise a distal strap aperture adapted to engage the strap to enable the flexible light treatment head to be maintained in position along a patient. In an embodiment, the flexible light treatment head may further comprise a knob to engage the strap to enable the flexible light treatment head to be maintained in position along a patient. In an embodiment, the knob may be provided on the hinge apparatus.

In a further aspect, each light source module may comprise one or more light emitting elements. In an embodiment, the light emitting elements may comprise light emitting diodes. In an embodiment, the light emitting elements may comprise LASERs. In an embodiment, each light source module may comprise a heat sink.

BRIEF DESCRIPTION OF THE DRAWINGS

The features of the invention will become more apparent in the following detailed description in which reference is made to the appended drawings wherein.

DETAILED DESCRIPTION OF THE INVENTION

The present invention provides a flexible light treatment head having a hinge apparatus along a flexing edge thereof. In one aspect, a corresponding hinge apparatus is provided along another flexing edge of the flexible light treatment head.

Figure 1:
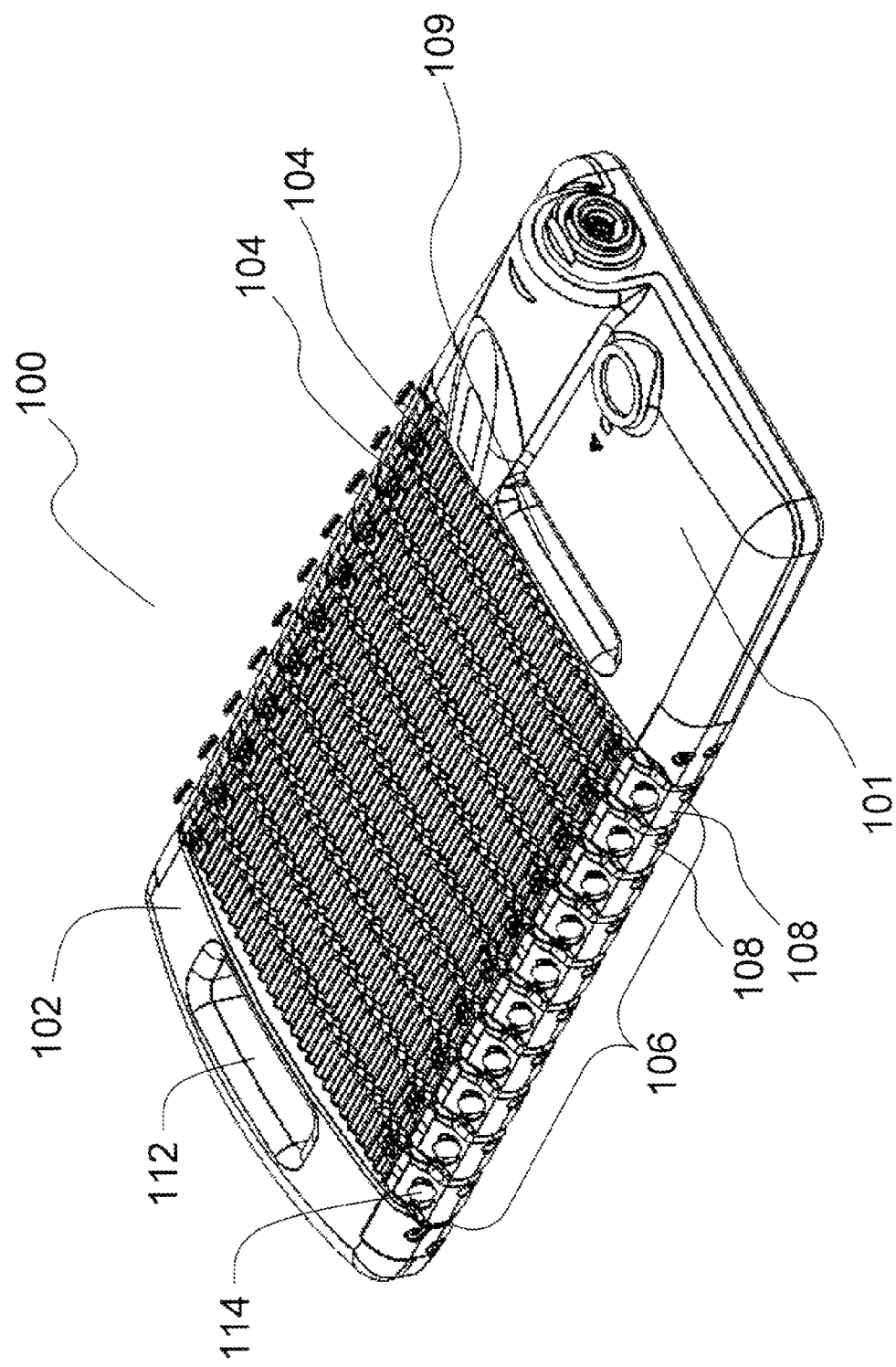
FIG. 1 is a front perspective view of a flexible light treatment head.
Figure 2:
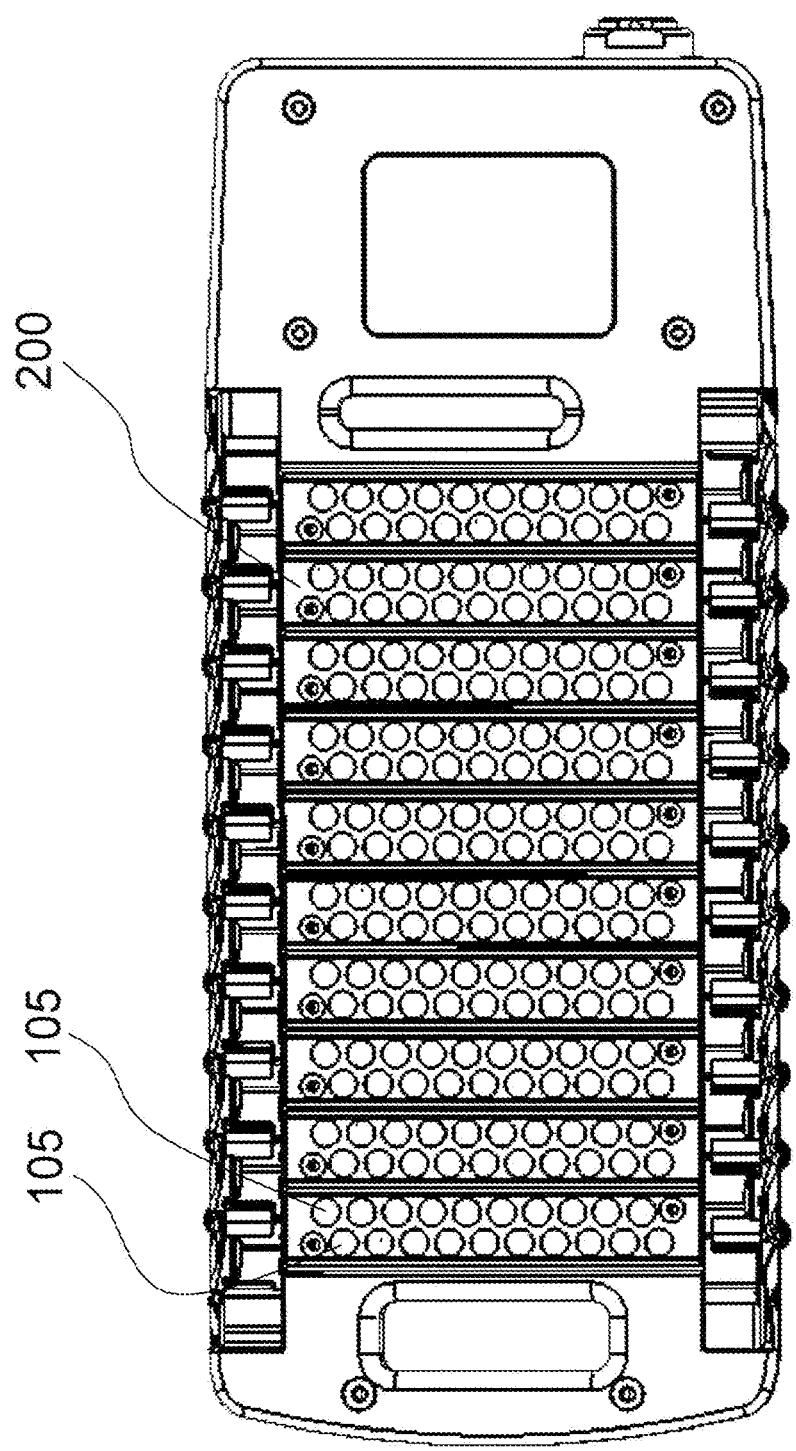
FIG. 2 is a bottom plan view of the flexible light treatment head.

Referring now to FIGS. 1 and 2, a flexible light treatment head (100) comprises a control module (101) and one or more light source modules (104) interconnected by a hinge apparatus (106). The hinge apparatus (106) is disposed along a flexing edge of the flexible light treatment head (100). The hinge apparatus (106) comprises a plurality of hinge joints (108).

Each light source module (104) may comprise one or more light emitting elements (105) disposed along a treatment surface (200) of the light source module for providing light therapy. In use, the light emitting elements (105) are placed in contact, or nearly in contact, with a patient's skin in proximity of the condition being treated.

In one aspect, the light emitting elements (105) comprise light emitting diodes (LED). In another aspect, the light emitting elements (105) comprise LASER. In yet another aspect, the light emitting elements (105) comprise any combination of LED and LASER. In additional aspects, it will be appreciated that any light emitting element (105) providing the desired therapeutic effect may be provided.

Typically, the wavelength and intensity of light emitted by such light emitting elements (105) is relevant to such therapeutic effect. In a specific embodiment, light having a 660 nm wavelength is applied. In another embodiment, light having a wavelength of 840 nm is applied. Combinations can also be applied. In specific embodiments, 660 nm light is provided at 750 mW total output power, which can be provided with approximately 180 LEDs, for example. In another embodiment 840 nm light is provided at 1500 mW of total output power, which can be provided with approximately 180 LEDs. In other embodiments 240 LEDs of 660 nm light provides 1000 mW and 240 LEDs of 840 nm light provides 2000 mW. Other output intensities are possible. Additionally, light emitting elements emitting light at other wavelengths could be provided, in particular to provide for different types of treatments.

In the particular embodiment shown in FIG. 2, each light source module (104) comprises twenty light emitting elements. In this particular embodiment, ten light source modules (104) are provided. In other embodiments, the treatment surface may correspond to an array of two to fifty light source modules. It will be appreciated that the light source modules could have differing numbers of light emitting elements.

Figure 3B:
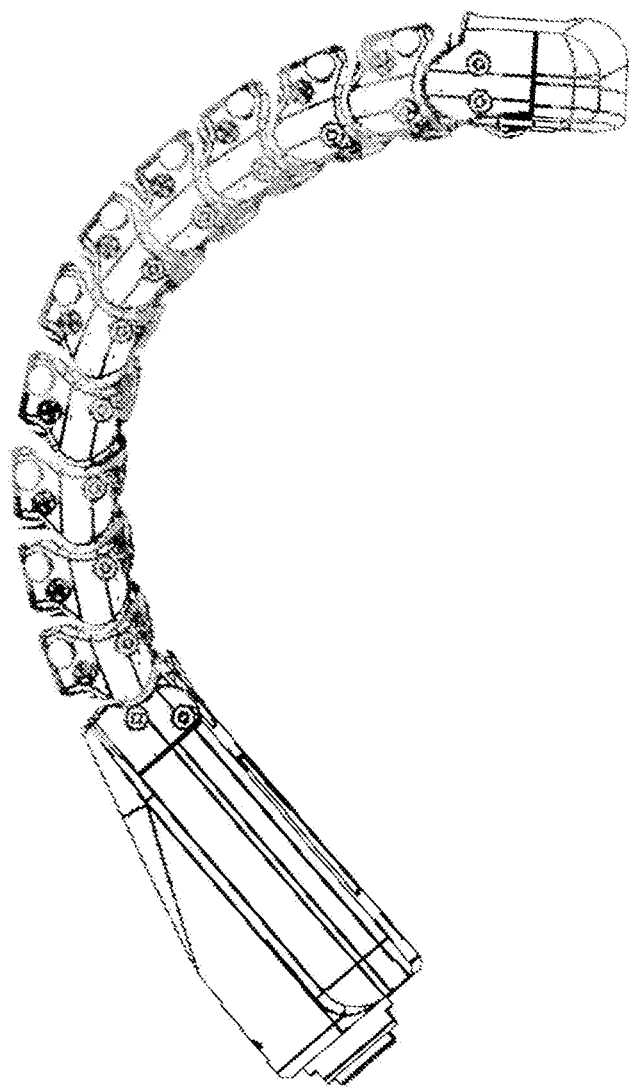
FIG. 3 shows a side view of flexible light treatment head.
Figure 3C:

Referring now to FIG. 3, a hinge apparatus (106) is shown. The hinge apparatus (106) enables the flexible light treatment head (100) to be flexed both inwardly (concavely) and outwardly (convexly) with reference to the treatment surface (200). The hinge apparatus is shown as being unflexed in FIG. 3A, flexed concavely in FIG. 3B and flexed convexly in FIG. 3C. The flexing angle and flexing radius can be configured by providing a suitable hinge apparatus, which is described more fully below. In a particular embodiment, the hinge apparatus (106) enables a radius of curvature of 20 mm concavely and 87 mm convexly, with reference to the treatment surface (200).

Furthermore, the hinge apparatus (106) preferably can be flexed concavely along a portion of the treatment surface and convexly along another portion of the treatment surface, for example to define an S-shape or wave-shape when viewed from a side profile. It will be appreciated that the number of regions of alternating flexing can be increased for a flexible light treatment head (100) with relatively more light source modules.

Figure 4:
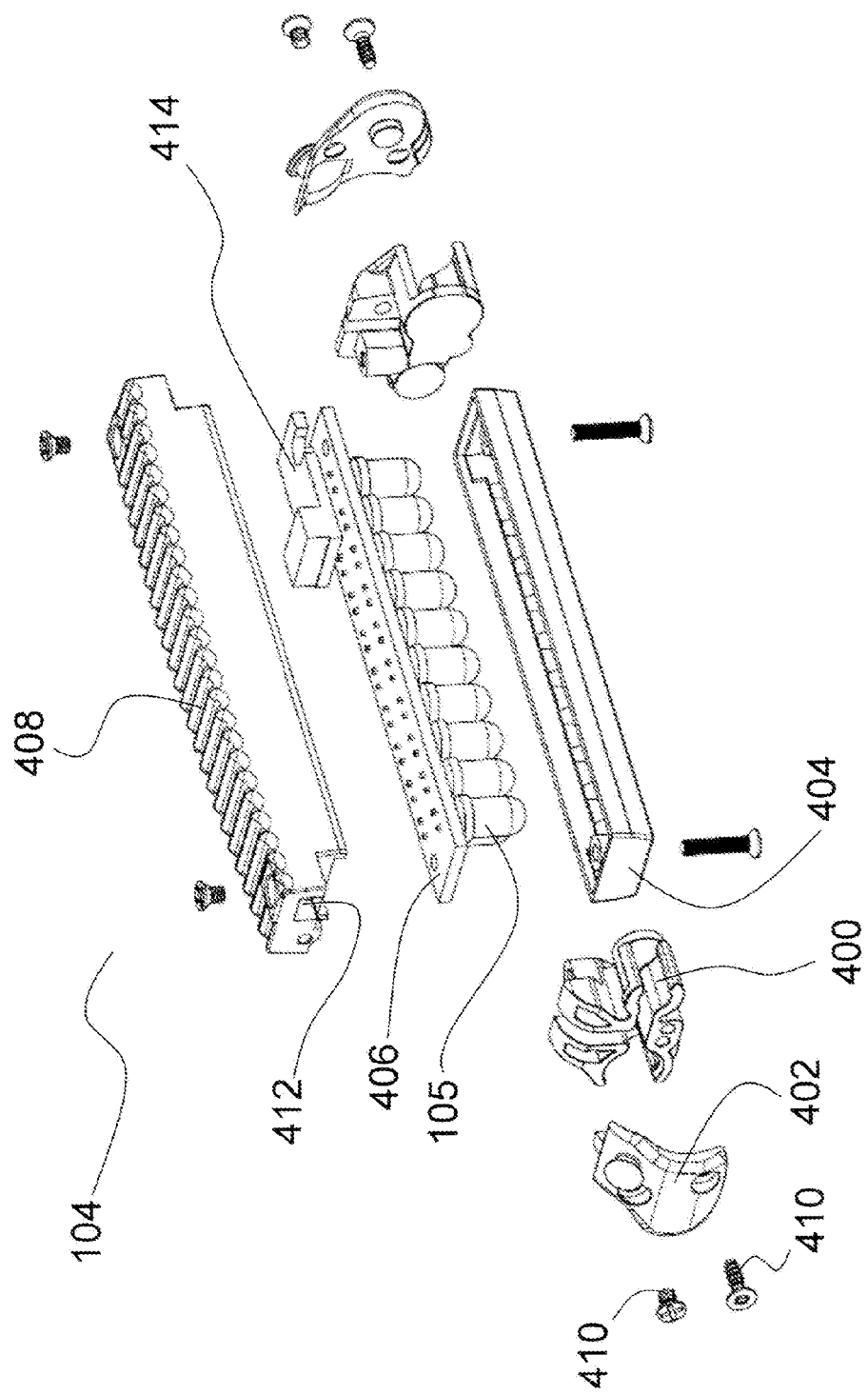
FIG. 4 is an exploded view of a light source module of the flexible light treatment head.

The hinge apparatus (106) is preferably unbiased and retains the desired flexing angle without requiring an additional mechanical positioning or holding means. Thus, the preferred hinge apparatus (106) allows the flexible light treatment head (100) to lie in substantial contact with the skin in the entire treatment area, including on contoured areas of the body such as the leg, neck, arm, back, etc. without requiring such an additional mechanical positioning or holding means Referring now to FIG. 4, a more detailed view of the hinge joint (108) and the light source module (104) is provided. The light source module (104) comprises an optical window (404), a circuit board (406) disposed above the optical window (404) and comprising circuitry sufficient to drive the light emitting elements (105) of the light source module (404), a heat sink body (408) disposed above the circuit board (406) operable to dissipate heat therefrom, and a plurality of light emitting elements (105) depending from the circuit board toward the optical window (404). The optical window (404) comprises a plurality of apertures or transparent or translucent portions enabling light emitted from the light emitting elements (105) to be emitted to the treatment surface (200). The heat sink body (408) and optical window (404) may be affixed to provide an enclosure. The light source module (104) may be assembled using screws (410) that bind the optical window to the heat sink body (408), with the circuit board being held, securely by the screws, other retaining elements provided in the heat sink body (408) and/or optical window (404), or by friction fit between the heat sink body (408) and optical window (404). The screws are selected to provide suitable clamping between the heatsink body and the circuit board to maximize heat dissipation. Thermal vias and/or large copper pads may additionally be provided in the circuit board to maximize heat dissipation.

The hinge assembly abuts one end of the light source module, which is a flexing edge of the flexible light treatment head (100). A corresponding hinge assembly may be provided along the other (opposite) flexing edge of the light source module for increased rigidity and/or increasing wiring capacity. For each light source module (104), the hinge assembly comprises a hinge joint (400) and may further comprise a hinge joint cover (402) disposed along an outer surface of the hinge joint (400) opposite the surface of the hinge joint abutting the light source module (104). The hinge joint cover (402) may be affixed to the hinge joint (400) by one or more screws, which may further affix the hinge assembly to the light source module (104).

In another embodiment, the hinge joints (400) may be integrally formed with the optical window (404) or heat sink body (408).

Figure 5:
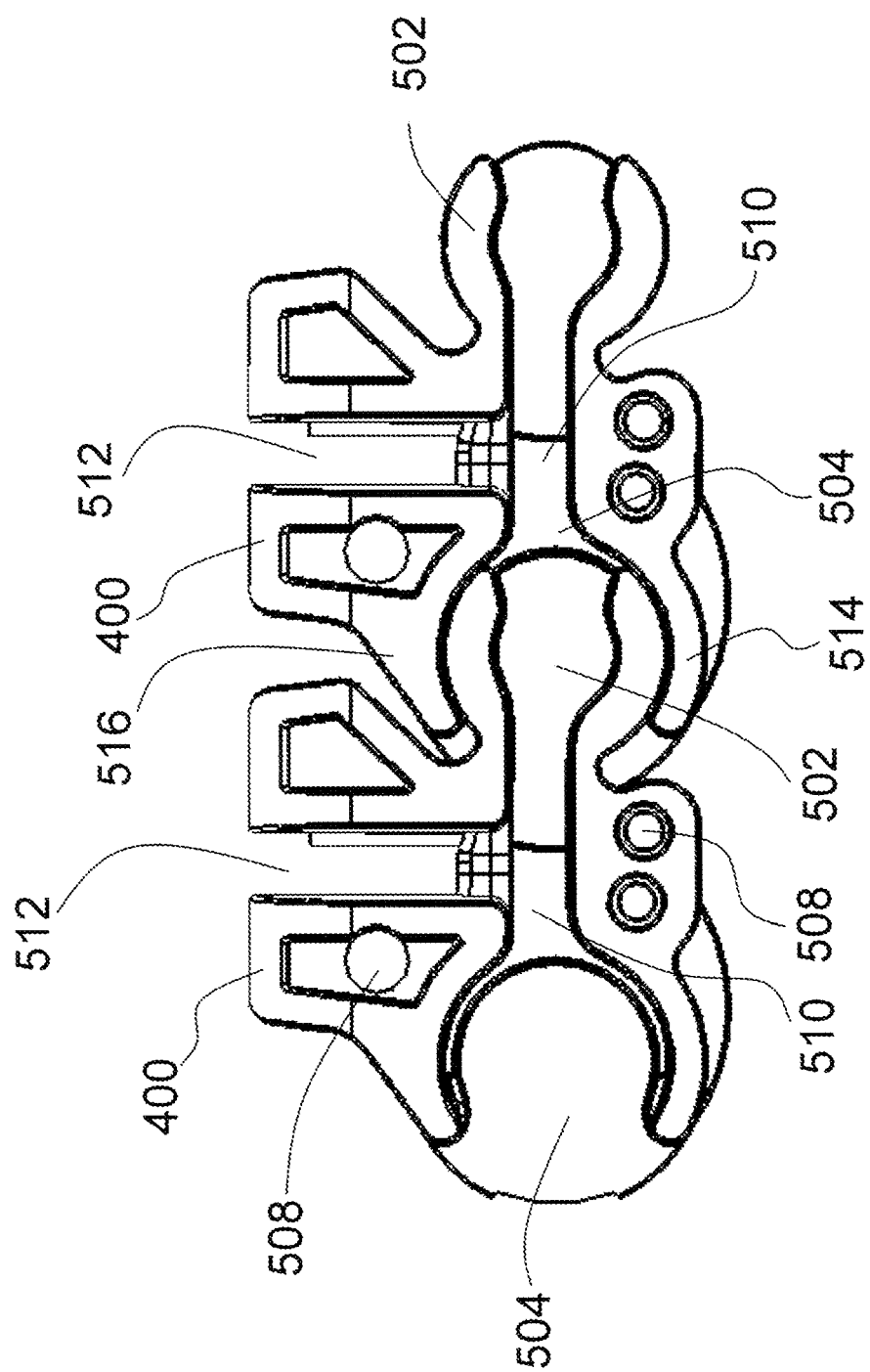
FIG. 5 is a side view of two adjacent hinge joints.

Referring now to FIG. 5, a close up view of two hinge joints is provided. The hinge joints (400) are substantially identical, and comprise a first end (502) and a second end (504), the first end (502) adapted to fit rotatably in a corresponding second end (504) of an adjacent hinge joint (400). For example, the first end may have an outer surface defining, in rotation, a cylinder of a particular circumference and the second end may have an inner surface forming a cylinder substantially equal but slightly larger in circumference that the outer surface of the first end, the slightly larger circumference enabling movement therebetween. While the inner surface of the second end is preferably cylindrical, the outer surface of the first end could be of any form that, in rotation, defines a cylinder. For example, the outer surface could be formed by a plurality of posts positioned to define the desired circumference. The hinge joints (400) allow for one degree of freedom rotationally so that the hinge apparatus (106) does not twist significantly along the common longitudinal axis of the hinge joints, hence providing substantial structural rigidity for the flexible light treatment head (100).

The control module (101) and strap adaptor (102) comprise a hinge joint or portion of a hinge joint to mate with a hinge joint of an adjacent light source module (104).

In one aspect, the hinge joint (400) enables different inward (concave) and outward (convex) flexing angles. In the embodiment shown in FIG. 5, for example, each hinge joint comprises a first flange (514) along the second end thereof to limit the movement of the first end of an adjacent hinge joint relative to the second end of the hinge joint to limit concave flexing. The hinge joint may comprise a second flange (516) to correspondingly limit convex flexing. It will be appreciated that the flanges could be provided at the first end of the hinge joint.

It will be appreciated that the light source modules may be dimensioned to further limit the flexing angles. For example, the depth of the optical window and the heat sink bodies, along with the space between adjacent light source modules, may limit the flexing angles as adjacent optical windows and/or heat sink bodies may come into contact during flexing.

The hinge joint (400) further comprises a head wiring channel (510) disposed from the first end to the second end. The head wiring channel (510) is continuous when two or more hinge joints are connected to one another, including at the extent of flexing the head both concavely and convexly. The head wiring channel (510) receives electrical wiring for driving the light emitting elements of each light source module.

A module wiring channel (512) extends from the head wiring channel (510) to the light source module. In the embodiment shown on FIG. 5, the module wiring channel (512) is disposed at an angle substantially perpendicular to the head wiring channel (510). Wiring placed in the head wiring channel (510) can be routed through the head wiring channel (510) to the light source module. In the light source module (104) shown in FIG. 4, for example, the heat sink body (408) has an aperture (412) disposed along at least one side thereof that enables wiring to be inserted into the light source module (104). This aperture could alternatively be disposed along the side of the optical window or between the heatsink and optical window.

The hinge joint cover (402) encloses the head wiring channel and module wiring channel. Thus, wires encased therein during normal operation of the flexible light treatment head have a decreased likelihood of accidental damage. Since the electrical wires are enclosed along the center of the hinge apparatus (106) as opposed to the sides, the compressive and tensile stresses incurred along the wire as the flexible light treatment head (100) is flexed are also reduced. The hinge joints (400) may be manufactured using a material which withstands corrosion or other damage so they may be cleaned with a medical grade disinfecting cloth.

The hinge joint may further comprise one or more apertures (508) disposed therethrough for receiving the screws (410). As can be appreciated, as the hinge joint cover can be affixed to the hinge joint by the screws, any one hinge joint cover can be selectively removed for diagnosing a fault in any particular light source module or for repairing any light source module and/or wiring fault. Furthermore, the present invention enables any particular hinge to be replaced without affecting the remaining hinge assembly.

The features just described offer various benefits including improved serviceability and customizability. For example, in the event that one or more light source module (104) has malfunctioned, the electrical wires corresponding to the modules may be easily accessed by removing the hinge joint cover (402). The malfunction may then be diagnosed. In another scenario, it may have been determined that one or more light source modules (104) need to be replaced. In this case, the hinge apparatus (106) can be partially disassembled so that said malfunctioning light source modules (104) can be substituted with new light source modules (104).

In one aspect, the control module (101) comprises circuitry sufficient to control the electrical operation of the flexible light treatment head (100). The control module may, for example, comprise a controller and supporting circuitry that are electrically connected to each light source module via wiring routed through the hinge assembly. In one aspect, each light source module is electrically substantially identical and connected to the control module (101) in parallel. Such an implementation enables at least some light source modules (104) to remain operational even if a particular malfunction may occur in one or more other light source modules (104).

The circuit board (406) of each light source module (104) may comprise a thermistor circuit (not shown). The controller may obtain the output of the thermistor circuit to determine the temperature of each light source module (104) in operation. The controller may selectively disable any one or more of the light source modules that reach a temperature over a configured threshold to prevent discomfort or trauma to the patient.

The circuit board (406) of each light source module (104) may further comprise a circuit diagnostic element (414). The circuit diagnostic element may, for example, comprise a sensing circuit, such as a resistor, for example, enabling the controller to obtain a voltage or current measurement relating to the light emitting elements of the light source module (104). For example, the light emitting elements (105) on a circuit board (406) may be connected in a set of parallel circuits. In a particular embodiment, twenty LEDs may be arranged in four parallel circuits each comprising five LEDs in series. The circuit diagnostic element (414) may be operable to determine the voltage of each series circuit. This information can be transmitted, in analog or digital form, to the control module. Thus, the controller may detect a malfunctioning light source module and may selectively disable any one or more of the light source modules that are malfunctioning.

Figure 6:
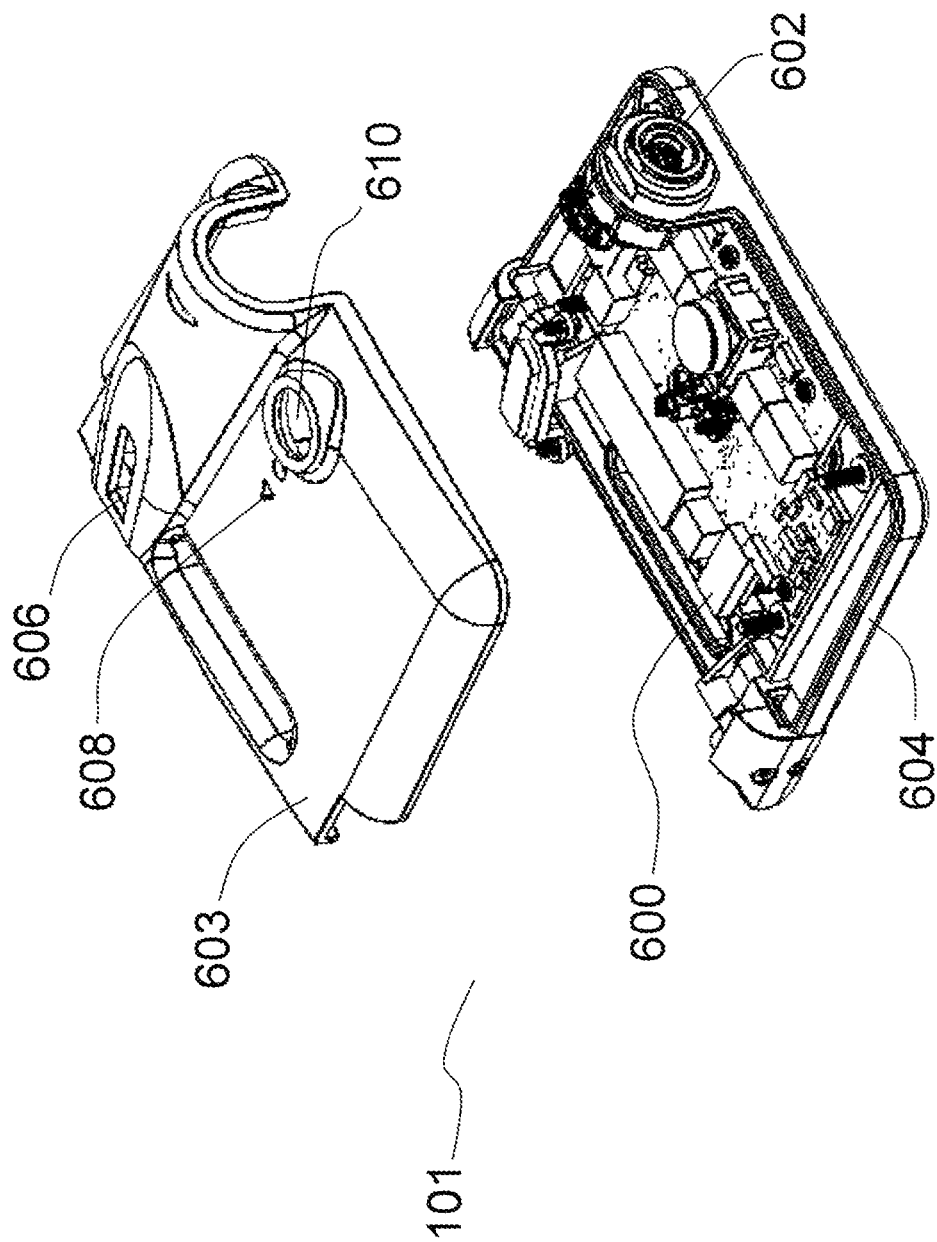
FIG. 6 is an exploded view of a control module of the flexible light treatment head.

A more specific embodiment of the control module (101) is shown in FIG. 6. The control module (101) may comprise a controller (600), top enclosure (603), bottom enclosure (604), connection port (602), a model window (606), status indicators (608), and a start/stop button (610). The status indicators may be used to indicate whether the flexible light treatment head is on or off, or whether the light emitting elements are enabled or disabled. The controller (600) supplies power to the light source modules (104), records light source module (104) usage data and monitors the temperature of the light source modules (104) to ensure patient contact temperature requirements are met. The controller (600) may turn on or off a light source module (104) whose temperature has exceeded preset limits. The controller (600) may also detect light emitting element failures by monitoring the sensing circuit.

The control module (101) may further comprise a warning window or label to provide required information, such as that required by a regulatory authority.

An external treatment controller (not shown) may provide power and/or instructions to the controller for a particular treatment via the connection port (602).

The flexible light treatment head (100) may further comprise a strap adaptor (102) disposed along one end of the flexible light treatment head (100). The strap adaptor (102) is preferably disposed along an end of the flexible light treatment head (100) opposite the control module (101) with the one or more light source modules (104) disposed therebetween. The strap adaptor (102) comprises a distal strap aperture (112) adapted to engage a strap. For example, a strap can be coupled to the flexible light treatment head (100) by affixing it to the distal strap aperture (112).

In one aspect, the control module (101) comprises a proximal strap aperture (109) adapted to engage the strap. For example, the strap can also be coupled to the flexible light treatment head (100) by affixing it to the distal strap aperture (112). Thus, a strap can be strapped from the proximal strap aperture, around a patient's body part, and to the distal strap aperture. This can be beneficial if gravity alone is not sufficient to maintain the position of the flexible light treatment head (100) during operation.

The strap adaptor (102), the distal strap aperture (112) or the proximal strap aperture (109) may further be used to hang the flexible light treatment head when not in use.

In another aspect, one or more of the light source modules (104) may comprise a knob (114). A suitable strap may comprise one or more apertures operable to engage the knob (114). This can be beneficial if the body part being treated is not suitable for using the two strap apertures (e.g., the body part is not cylindrical in the plane of treatment). The knob (114) may be provided on the hinge joint covers (402).

Figure 7A:
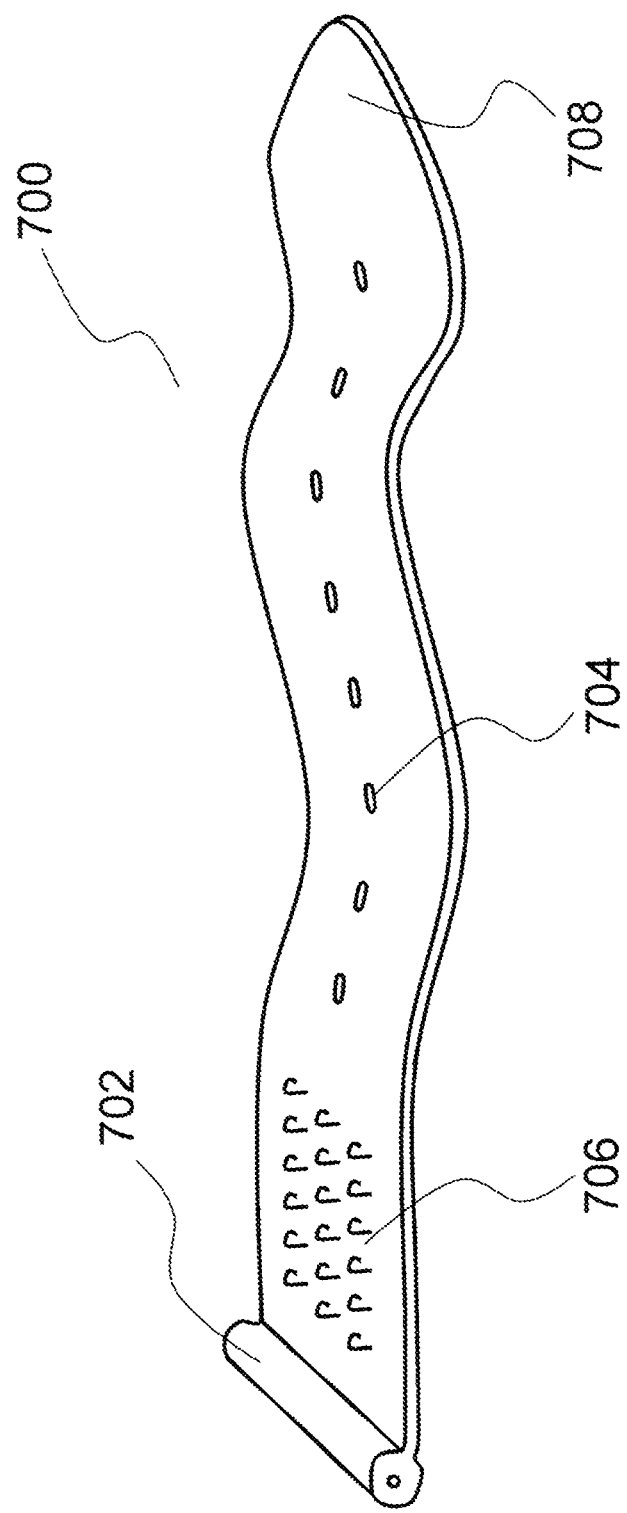
FIG. 7 is a front perspective view of a strap that can be affixed to the flexible light treatment head.

Referring now to FIG. 7a, a strap is shown. The strap (700) can be affixed to the flexible light treatment head (100) at each end thereof, for example at the proximal strap adaptor, distal strap adaptor or any of the knobs. For example, the strap may comprise a fastener (702) at each end thereof to enable each end to be strapped to the strap apertures. The fastener may, for example, comprise Velcro, buttons, or other fasteners.

Figure 7B:
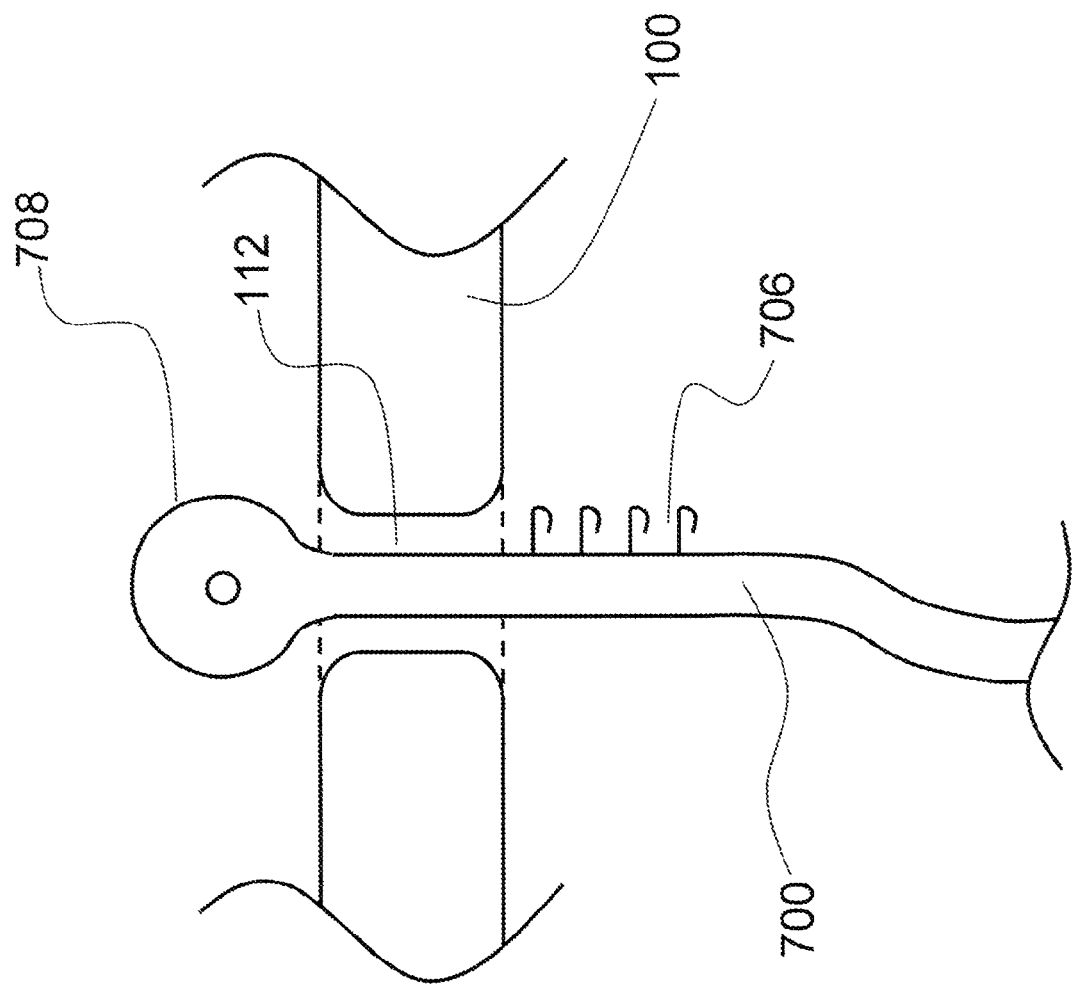

Referring now to FIG. 7b, the strap may alternatively comprise a stopper (708) at one end thereof wherein the stopper (708) is larger in at least one dimension than the proximal strap adaptor (109) and/or the distal strap adaptor (112). In this embodiment, the strap can be woven through either strap adaptor from the end opposite of the stopper such that the stopper is prevented from passing through the strap adaptor.

The strap may be a stretchable fabric or comprise a stretchable portion. For example, the strap may comprise a Vel-stretch material.

The strap may further comprise one or more apertures (704) through which a knob can be received. Optionally, the strap can be affixed to the flexible light treatment head (100) using one or more apertures and one or more corresponding knobs, with or without one or two of the strap apertures or avoiding use of the strap apertures completely.

Although the invention has been described with reference to certain specific embodiments, various modifications thereof will be apparent to those skilled in the art without departing from the invention as outlined in the claims appended hereto. The entire disclosures of all references recited above are incorporated herein by reference.

What is claimed is:

1. A flexible light treatment head comprising a plurality of light source modules arranged in seriatim along a major axis of said head, adjacent ones of the modules being interconnected by hinges, each of said the modules comprising a middle portion, a first hinge and a second hinge; the middle portion comprising one or more lighting elements; the first hinge and the second hinge respectively positioned at an outer left-side edge and an outer right-side edge of the middle portion and separated by the middle portion; each of the first hinge and the second hinge comprising a receiving portion and a protruding portion, receiving portions of a first hinge and a second hinge of a first given module configured to rotatably connect to protruding portions of a first hinge and a second hinge of a second given module that is connected to one side of the first given module; and the protruding portions of the first hinge and the second hinge of the first given module configured to rotatably connect to receiving portions of a first hinge and a second hinge of a third given module that is connected to another side of the first given module; wherein for each of the modules, each one of the first hinges defines therein a first channel that extends between the receiving portion to the protruding portion, and a combination of the first channels within the first hinges, which are connected in seriatim, form a continuous channel that extends along the outer left-side edge of the flexible light treatment source; wherein each of the first hinges comprise a second channel extending substantially perpendicularly from the first channel; and a wire extends within the continuous channel and the second channel.

2. The flexible light treatment head of claim 1, wherein for each of the modules, the middle portion, the first hinge and the second hinge are separate components assembled together.

3. The flexible light treatment head of claim 1, wherein for each of the modules, each one of the second hinges defines therein a first channel that extends between the receiving portion to the protruding portion, and a combination of the first channels within the second hinges, which are connected in seriatim, form a continuous channel that extends along the outer right-side edge of the flexible light treatment source; and a wire extends within the continuous channel.

4. The flexible light treatment head of claim 3, wherein each of the second hinges comprise a second channel extending substantially perpendicularly from the first channel.

5. The flexible light treatment head of claim 1, wherein the hinges of the flexible light treatment head provide a radius of curvature of 20 mm concavely and 87 mm convexly with reference to a treatment surface of said flexible light treatment head.

6. The flexible light treatment head of claim 1, further comprising a hinge joint between each interconnected hinge, and a hinge joint cover disposed along an outer surface of each hinge joint.

7. The flexible light treatment head of claim 6, wherein the hinge joint cover is removable to diagnose and repair the flexible light treatment head.

8. The flexible light treatment head of claim 1, wherein the flexible light treatment head further comprises a proximal strap aperture adapted to engage a strap.

9. The flexible light treatment head of claim 8, wherein the flexible light treatment head further comprises a distal strap aperture adapted to engage the strap to enable the flexible light treatment head to be maintained in position along a patient.

10. The flexible light treatment head of claim 8, wherein the flexible light treatment head further comprises a knob to engage the strap to enable the flexible light treatment head to be maintained in position along a patient.

11. The flexible light treatment head of claim 1, wherein the light emitting elements comprise light emitting diodes.

12. The flexible light treatment head of claim 1, wherein the light emitting elements comprise LASERs.

13. The flexible light treatment head of claim 1, wherein each light source module comprises a heat sink body.

14. A flexible light treatment head comprising a plurality of light source modules arranged in seriatim along a major axis of said head, adjacent ones of the modules being interconnected by a first hinge assembly and a second hinge assembly, one of the first and the second hinge assemblies located on an outer left edge of the flexible light treatment head, and the other one of the first and the second hinge assemblies located on an outer right edge of the flexible light treatment head; each of the modules comprising a first hinge and a second hinge that are separated by a middle portion; the middle portion comprising one or more lighting elements; the first hinge assembly comprising the first hinges connected in seriatim together, each of the first hinges comprising a protruding portion and a receiving portion to respectively connect with a receiving portion and protruding portion of other adjacent first hinges; the second hinge assembly comprising the second hinges connected in seriatim together, each of the second hinges comprising a protruding portion and a receiving portion to respectively connect with a receiving portion and a protruding portion of other adjacent second hinges; each of the first hinges defines therein a first channel that extends between the receiving portion and the protruding portion, and the first hinges connected together in seriatim form a continuous first channel that extends along the first hinge assembly; wherein each of the first hinges comprise a second channel extending substantially perpendicularly from the first channel; and a wire extends within the continuous first channel and the second channel.

15. The flexible light treatment head of claim 14 wherein each of the second hinges defines therein a channel that extends between the receiving portion and the protruding portion, and the second hinges connected together in seriatim forms a continuous second channel that extends along the second hinge assembly.

16. A flexible light treatment head comprising a plurality of light source modules arranged in seriatim along a major axis of said head, adjacent ones of the modules being interconnected by a first hinge assembly and a second hinge assembly, one of the first and the second hinge assemblies located on an outer left edge of the flexible light treatment head, and the other one of the first and the second hinge assemblies located on an outer right edge of the flexible light treatment head; each of the modules comprising a first hinge and a second hinge that are separated by a middle portion; the middle portion comprising one or more lighting elements; the first hinge assembly comprising the first hinges connected in seriatim together, each of the first hinges comprising a protruding portion and a receiving portion to respectively connect with a receiving portion and protruding portion of other adjacent first hinges; the second hinge assembly comprising the second hinges connected in seriatim together, each of the second hinges comprising a protruding portion and a receiving portion to respectively connect with a receiving portion and protruding portion of other adjacent second hinges; each of the first hinges defines therein a first channel that extends between the receiving portion and the protruding portion, and the first hinges connected together in seriatim form a continuous first channel that extends along the first hinge assembly; each of the first hinges comprise a removable cover positioned over the first channel defined in each of the first hinges, the removable cover having one side convex shaped and an opposite side concave shaped to facilitate multiple ones of the removable cover nested together along the length of the first hinge assembly; wherein each of the first hinges comprise a second channel extending substantially perpendicularly from the first channel; and a wire extends within the continuous first channel and the second channel.

17. The flexible light treatment head of claim 15 wherein each of the second hinges defines therein a channel that extends between the receiving portion and the protruding portion, and the second hinges connected together in seriatim forms a continuous second channel that extends along the second hinge assembly; each of the second hinges further comprises the removable cover; and multiple ones of the removable cover are nested together and are positioned along the length of the second hinge assembly.

* * * * *